(12) United States Patent
Stern et al.

(10) Patent No.: US 6,198,961 B1
(45) Date of Patent: Mar. 6, 2001

(54) INTERVENTIONAL RADIO FREQUENCY COIL ASSEMBLY FOR MAGNETIC RESONANCE (MR) GUIDED NEUROSURGERY

(75) Inventors: Benjamin R. Stern, Willoughby Hills; John D. Schellenberg, Cleveland; David A. Lampman, Eastlake, all of OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/190,635

(22) Filed: Nov. 12, 1998

(51) Int. Cl.[7] .................................................. A61B 5/055
(52) U.S. Cl. ............................................. 600/422; 324/318
(58) Field of Search ................................... 600/422, 421, 600/417; 324/318, 321; 606/130

(56) References Cited

U.S. PATENT DOCUMENTS

| | | | | |
|---|---|---|---|---|
| 4,791,372 | * | 12/1988 | Kirk et al. | 324/318 |
| 4,923,459 | * | 5/1990 | Nambu | 606/130 |
| 4,968,936 | * | 11/1990 | Darrasse et al. | 324/318 |
| 5,261,403 | * | 11/1993 | Saito et al. | 128/653.2 |
| 5,274,332 | * | 12/1993 | Jakolski et al. | 324/318 |
| 5,519,321 | * | 5/1996 | Hagen et al. | 324/318 |
| 5,706,812 | * | 1/1998 | Strenk et al. | 128/653.5 |
| 5,945,827 | * | 8/1999 | Gronauer et al. | 324/318 |
| 5,971,997 | * | 10/1999 | Guthrie et al. | 606/130 |
| 6,011,393 | * | 1/2000 | Kaufman et al. | 324/318 |
| 6,021,343 | * | 2/2000 | Foley et al. | 600/429 |

* cited by examiner

Primary Examiner—Marvin M. Lateef
Assistant Examiner—Shawna J. Shaw
(74) Attorney, Agent, or Firm—Fay, Sharpe, Fagan, Minnich & McKee, LLP

(57) ABSTRACT

A diagnostic imaging apparatus such as a magnetic resonance imaging (MRI) device includes a gradient coil assembly (34) and an RF coil (36) disposed proximate pole faces (30, 32). An interventional head coil assembly (40) includes a base (90), a head frame housing (96) including at least one first conductor (130) associated therewith, a first mount (94) that connects the head frame housing (96) to the base (90), a bridge housing (98) including at least one second conductor (142) associated therewith, and a second mount (100) that connects the bridge housing (98) to the head frame housing (96) thereby coupling the at least one first conductor (130) to the at least one second conductor (142) to form a surface coil for use in imaging an object attached to the head frame housing (96).

22 Claims, 7 Drawing Sheets

INTERVENTIONAL RADIO FREQUENCY COIL ASSEMBLY FOR MAGNETIC RESONANCE (MR) GUIDED NEUROSURGERY

BACKGROUND OF THE INVENTION

The present invention relates to the magnetic resonance (MR) art. It finds particular application in conjunction with an interventional radio frequency (RF) coil assembly for use in magnetic resonance guided neurosurgery, and will be described with particular reference thereto. However, it should be appreciated that the present invention may also find application in conjunction with other types of neurosurgical and diagnostic imaging systems.

When performing surgery on a patient's brain, the patient's head is usually held fixed by a head frame. Known head frames typically include a clamp or frame-like structure with several sharp pins that are anchored in the patient's skull in order to immobilize the frame-like structure relative to the patient's head. The head frame is connected to a surgical table by a series of links and joints that permit the head frame to be positioned with respect to the table with several degrees of freedom. By this means, the head frame can be positioned to hold the patient's head in a range of orientations to present the surgeon with an appropriate approach to the surgical field. However, access to the patient's head is still restricted by the head frame.

Conventional head frames include the designs of Ohio Medical (Cincinnati, Ohio.) and many other companies. The most common model is the Mayfield frame made by Ohio Medical and described in U.S. Pat. Nos. 4,169,478 and 5,269,034. The Mayfield frame is made from cast aluminum and is not MR compatible. In MR guided neurosurgery, the head frame must be made from an MR compatible material. Ohio Medical and Elekta Instruments (Atlanta, Ga.) both make radiolucent head frames for intraoperative x-ray or CT imaging. These products are made from a carbon fiber/epoxy composite and have been used for intraoperative MR imaging. An exemplary radiolucent head frame is described in U.S. Pat. No. 5,537,704.

When performing neurosurgery with MR guidance, a receive surface coil is used for local imaging of a patient's brain because a higher signal-to-noise ratio can be obtained than with a whole body RF coil. The surface coil is designed to be placed as close as possible to the patient's head to increase the signal to noise ratio. The surface coil is typically covered by a sterile bag or placed on the patient prior to applying sterile drapes. As with head frames, surface coils typically restrict access to the patient's head.

Research and development is presently being conducted on specific surface coil designs for use in MR guided neurosurgery. For horizontal field interventional MR, flexible surface coils, either of a single-solenoid or Helmholtz configuration are being contemplated. These coils would generally be used with the loops in the coronal plane, with a non-sterile loop below the patient's head and a sterile or sterile-bagged loop above the patient's head. For vertical field interventional MR, flexible single-solenoid surface coils are contemplated. These coils are oriented in the transverse plane, placed around the patient's head. The known surface coil designs are not easily sterilized.

Thus, in MR guided neurosurgery, both the head frame and the surface coil restrict access to the patient's head. Further, it is often difficult to position both the surface coil and the head frame so as to keep the region of interest in the sensitive volume of the surface coil and to allow sufficient access for surgery. If the surface coil has to be moved away from the anatomy of interest to allow space for the head frame or access for the surgeon, the signal to noise ratio will suffer.

The present invention contemplates a new and improved interventional radio frequency coil assembly for use in magnetic resonance guided neurosurgery that overcomes the above-referenced problems and others.

SUMMARY OF THE INVENTION

In accordance with one aspect of the present invention, there is provided a diagnostic imaging apparatus including a housing defining an examination region, a main field magnet that generates a temporally constant magnetic field through the examination region, a gradient assembly that induces gradient magnetic fields across the temporally constant magnetic field, a patient couch that positions an object to be imaged within the examination region, and an interventional head frame assembly positioned within the examination region. The head frame assembly includes a head frame housing attached to the object and having at least one first conductor therein, a first mount that supports the head frame housing or the patient couch, a bridge housing including at least one second conductor therein, and a second mount that attaches the bridge housing to the head frame housing and electrically couples the at least one first conductor to the at least one second conductor to form a surface coil for use in imaging an object held by the head frame.

In accordance with a second aspect of the present invention, there is provided an interventional head coil assembly. The interventional head coil assembly includes a base, a head frame housing including at least one first conductor associated therewith, a first mount that connects the head frame housing to the base; a bridge housing including at least one second conductor associated therewith, and a second mount that connects the bridge housing to the head frame housing thereby coupling the first conductor to the second conductor to form a surface coil for use in imaging an object attached to the head frame housing.

In accordance with a second aspect of the present invention, there is provided a method of performing neurosurgery with diagnostic imaging guidance. The method includes attaching a head frame housing to a patient's head, the head frame housing having a first conductor associated therewith, inserting a plurality of pins through a sterile drape positioned over the head frame housing and into engagement with a corresponding plurality of electrical connectors associated with the head frame housing; attaching a sterile bridge housing to the contact pins thereby coupling a second conductor associated with the bridge housing to the first conductor to form a surface coil, positioning the patient's head within an examination region of a diagnostic imaging system, and performing a diagnostic imaging procedure utilizing the surface coil.

One advantage of the present invention is the provision of a new and improved interventional head coil for use with a vertical field MR scanner.

Another advantage of the present invention is the provision of a new and improved interventional head coil that combines a split-top linear receive surface coil with an arc-type head frame.

Another advantage of the present invention is the provision of a new and improved interventional head coil that includes passive NMR fiducials for registering the images obtained with the coil to an image guided surgery system.

Another advantage of the present invention is the provision of a new and improved interventional head coil that combines an MR surface coil and a neurosurgical headframe into one device, allowing convenient positioning of the surface coil for MR guided neurosurgery.

Another advantage of the present invention is the provision of a new and improved interventional head coil that increases the access to the patient's head while maintaining proper positioning of a surface coil and therefore high signal-to-noise ratio.

Another advantage of the present invention is the provision of a new and improved interventional head coil that utilizes surface coil conductors to provide a substantial portion of the requisite strength and stiffness of the head frame.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
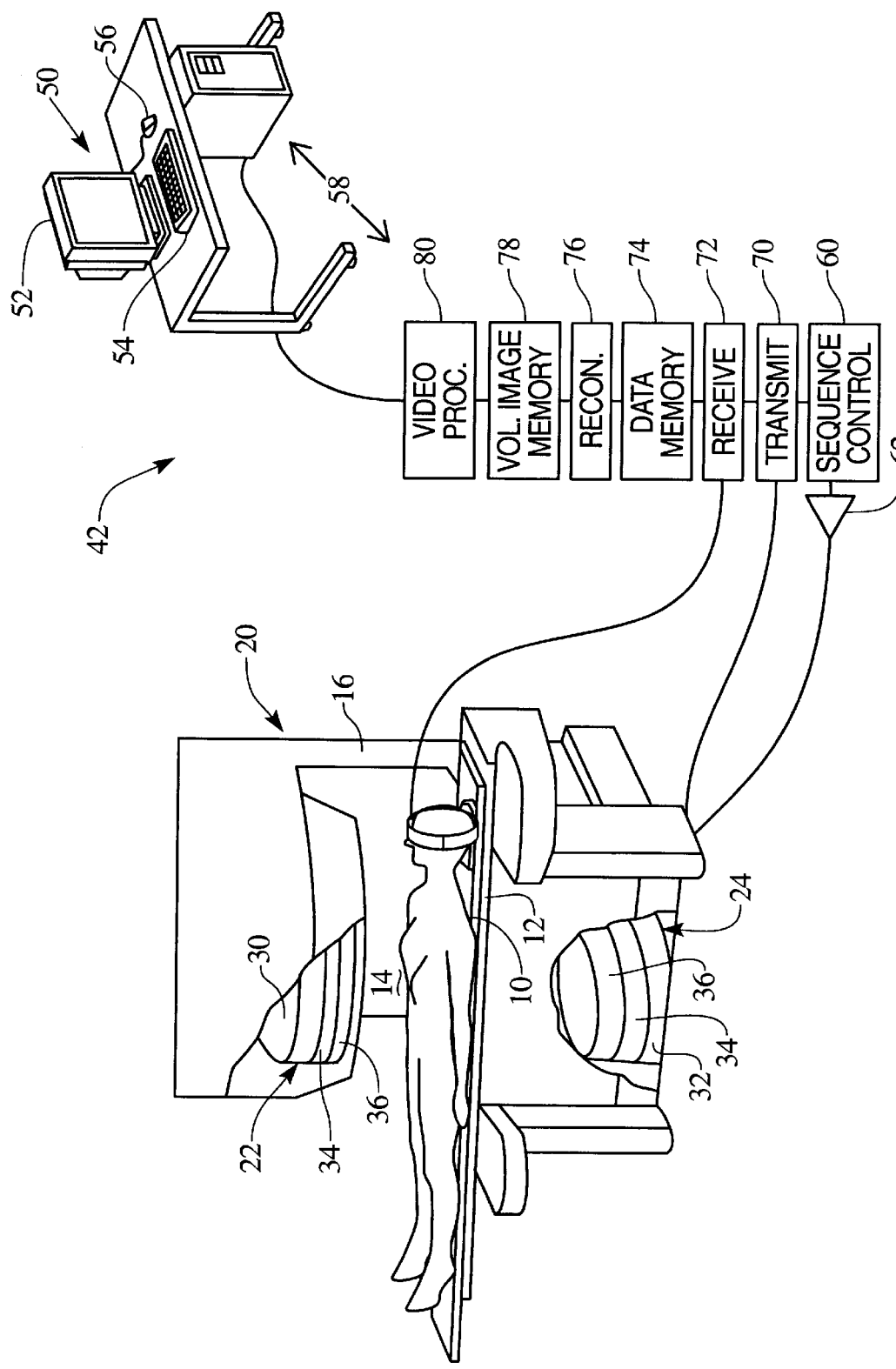
FIG. 1 is a diagrammatic illustration of an exemplary magnetic resonance (MR) imaging system for use with an interventional radio frequency (RF) coil assembly of the present invention.

With reference to FIG. 1, a support couch 10 is slidably mounted on a support frame 12. The support couch supports a patient or subject in an air gap 14 defined between pole faces of a C-shaped ferromagnetic flux path 16. The ferromagnetic flux path 16 includes a C-shaped ferromagnetic member 20 having a first end 22 and a second end 24. A first pole piece 30 and a second pole piece 32 at the first and second ends of the flux path, respectively, define the air gap 14 therebetween. The C-shaped member is configured to minimize the length of the ferromagnetic flux path while spacing the ferromagnetic flux path sufficiently from the gap to minimize distortion to a uniform, temporally constant magnetic field $B_0$ generated along a vertical axis in the air gap.

The ferromagnetic flux path can be solid, laminated, include an air core or the like. The ferromagnetic flux path can include flared ends toward the pole pieces to provide a smooth transition between the iron core and the larger cross-section pole pieces which may be circular, oval, rectangular, or the like.

The C-shaped member preferably consists of iron or an iron-cobalt alloy but may also consist of another metal, alloy or compound of the transition, rare-earth, and acitinide elements. In addition, various other configurations for the ferromagnetic flux path are contemplated including double-C shaped members, which define two return flux paths as well as configurations with a larger number of flux paths.

A whole body gradient coil assembly 34 includes x, y, and z-coils mounted on the pole pieces for generating gradient magnetic fields, $G_x$, $G_y$, and $G_z$. Preferably, the gradient coil assembly is a self-shielded gradient coil that includes primary x, y, and z-coil assemblies and secondary x, y, and z-coil assemblies. A whole body radio frequency coil 36 can be mounted between the upper and lower portions of the gradient coil assembly 34. An interventional radio frequency coil assembly 40 is removably mounted to the patient couch 10 within an examination region defined by the air gap 14.

Magnetic resonance electronics 42 selectively induce magnetic resonance of dipoles in the image region and process resultant received magnetic resonance signals to create an image or other diagnostic information. In particular, an operator interface and control station 50 includes a human-readable display, such as a video monitor 52, and an operator input means including a keyboard 54, a mouse 56, a trackball, light pen, or the like. A computer control and reconstruction module 58 includes hardware and software for enabling the operator to select among a plurality of preprogrammed magnetic resonance sequences that are stored in a sequence control memory. A sequence controller 60 controls gradient amplifiers 62 and a digital transmitter 70. The gradient amplifiers are connected to the gradient coil assembly 34 for causing the generation of the $G_x$, $G_y$, and $G_z$ gradient magnetic fields at appropriate times during the selected gradient sequence. The digital transmitter 70 causes the whole body radio frequency coil 36 to generate $B_1$ radio frequency field pulses at times appropriate to the selected sequence.

The resonance frequency signals from the interventional RF coil assembly 40 are demodulated by a digital receiver 72 and stored in a data memory 74. Data from the memory is reconstructed by a reconstruction or array processor 76 into corresponding volumetric image representations that are stored in corresponding portions of an image memory 78. A video processor 80, under operator control, converts selected portions of the volumetric image representation into slice images, projection images, perspective views, or the like as is conventional in the art for display on the video monitor 52.

Figure 2:
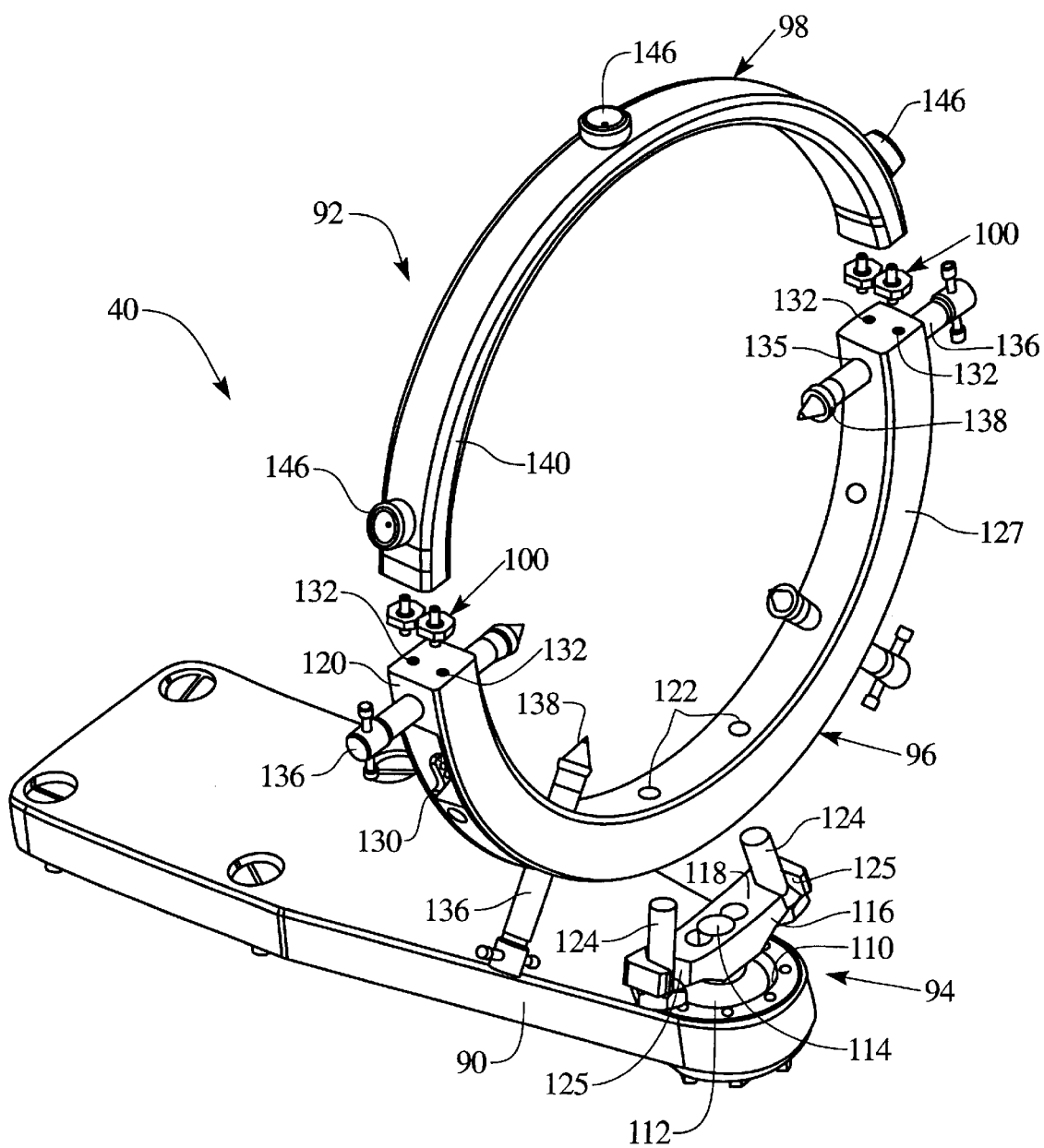
FIG. 2 is a perspective view of an interventional RF coil assembly that incorporates features of the present invention therein.

Referring now to FIG. 2, the interventional radio frequency coil assembly 40 includes a base 90, a head-frame assembly 92, and a first mount 94 that releasably secures the head-frame assembly 92 to the base 90. The head-frame assembly 92 includes a lower member or arc 96 that functions as a head frame, an upper member or bridge 98, and second mounting means, such as contact pins 100, for releasably securing the bridge 98 to the arc 96. The arc 96 not only functions as the head frame, but also cooperates with the bridge to form a surface coil integral with the head frame assembly 92.

The base 90 is adapted for releasable attachment to the patient couch 42 (FIG. 1). In the described embodiment, the first mount 94 includes a socket 110 associated with the base 90 for receiving a mutually conforming spherical member 112. A rod 114 extends from the spherical member 112 and supports a shoulder member 116. She shoulder member includes an upper surface 118 that conforms with a lower surface 120 of the arc 96. Attachment points such as tapped holes 122 extend radially at least partially through the arc 96. Pins 124 threadably engage with the tapped holes 122. The shank portions of each pin 124 releasably engage with notches 125 associated with the shoulder member 116. A locking means (not shown) selectively locks the spherical member 112 against the socket 110. Alternatively, the first mount 94 can include a clamp member 126 (FIG. 5) for engaging the arc 96. In either case, the first mount 94 permits the head frame assembly 92 to be positioned with respect to the table with several degrees of freedom. By this means, the arc 96 can be positioned to hold a patient's head in a range of orientations to present a surgeon with an appropriate approach to the surgical field.

Figure 3:
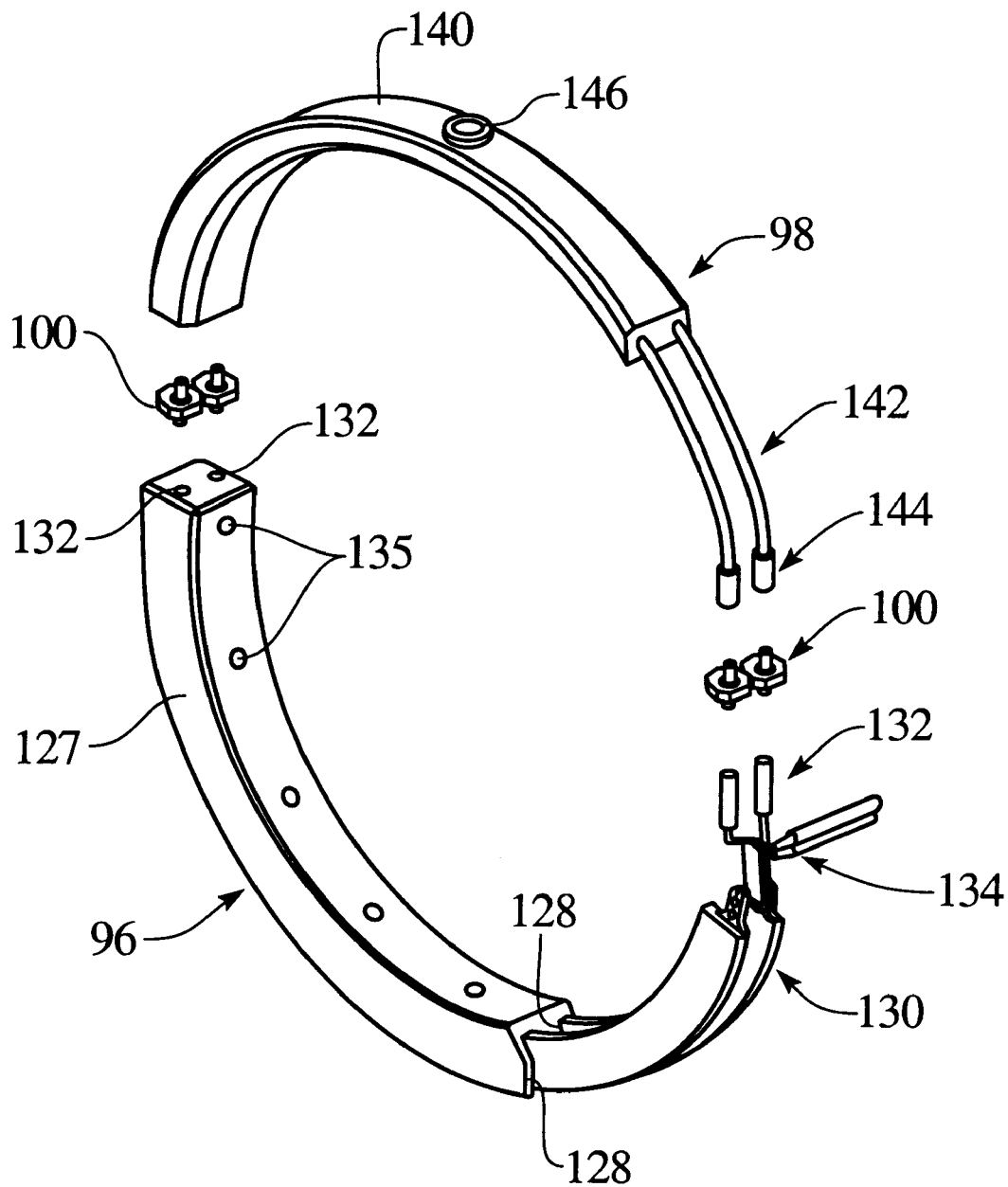
FIG. 3 is an exploded perspective view, partially cutaway, of a head frame portion of the interventional RF coil assembly of FIG. 2.

With continuing reference to FIG. 2, and particular reference to FIG. 3, the arc 96 includes a housing portion 127 having circumferentially extending slots 128 therein. The slots 128 receive lower surface coil conductors 130 (preferably two). The lower conductors 130 serve two functions; carrying the current of the surface coil, and acting as structural reinforcements. Lower contacts 132 are press fit or bonded into the arc housing and can be threaded to accept the contact pins 100.

The arc housing 127 is preferably fabricated from a high-performance MR compatible plastic material such as polyetherimide. The lower conductors 130 are preferably fabricated from a high-strength, high-conductivity copper alloy such as C18200. In the embodiment being described, the conductors contribute about 73% of the stiffness of the head-frame assembly 92. Due to the high stiffness and strength of the copper alloy conductors, the interventional head coil requires no more space than a standard head frame. The lower contacts 132 are also made from a high-strength, high-conductivity copper alloy, and are preferably gold plated to avoid changes in electrical resistance due to surface corrosion. The arc 96 also houses tuning electronics (not shown) and a feed point 134 by which the surface coil is attached to the MR scanner 10 vís-a-vís a pre-amplifier stage, etc.

The arc housing 127 includes several additional attachment points such as tapped holes 135 radial to the arc. The holes 135 are used for attaching screws 136 on which are mounted pins 138 that engage the patient's skull. The threaded holes 135 can also be used to attach conventional surgical accessories such as retractors, hand rests, and biopsy positioners to the head frame assembly 92.

The bridge 98 includes a housing portion 140 that encloses upper conductors 142 (preferably two) and upper contacts 144. The bridge is located within a sterile field when mounted to the arc vís-a-vís the contact pins 100. Thus, the bridge must be readily sterilizable, and therefore, must not include any geometry such as seams or joints, that would make sterilization difficult. In the described embodiment, the bridge 98 is manufactured by an insert molding process. In particular, the upper contacts 144, preferably fabricated from gold-plated copper alloy, are soldered to the upper conductors 142. The conductors 142 are fabricated from copper tubing that is bent into an accurate shape corresponding to the bridge. The conductor assemblies are then inserted into a mold, supported by pins mating with the upper contacts, and by other supports if needed. Then, an injection molding process may be used to inject a thermoplastic material, a reaction injection molding process may be used to inject a thermoset material, or a liquid resin casting process may be use to inject a liquid resin. Suitable materials for injection molding include polyetherimide, polyphenylsulfone and ABS. Suitable materials for reaction injection molding or liquid resin casting include polyurethane and epoxy. By this method, the conductors and contacts are completely encased in the housing material, and the bridge 98 can be easily sterilized.

Active or passive fiducial markers 146 are attached to the top of the bridge 98 to aid in registering the image data to an image guided surgery system. Active or passive fiducial markers can also be attached to the arc if desired. Passive fiducial markers can be fabricated from Santoprene (Advanced Elastomer Systems, Akron, Okio) or any other durable material that can be imaged by a MR scanner. In use, the field of view of the scanner is set to include the fiducials 146 on the bridge 98. When the image data is used by the image guided surgery system, the operator can point to the fiducials 146 with a navigation tool and select the fiducials in the image, thereby relating the image data coordinates to the image guided surgery system coordinates in a known manner.

Figure 4:
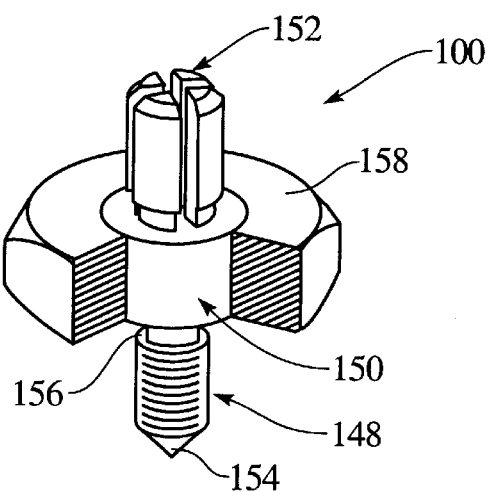
FIG. 4 is a perspective view, partially cutaway, of a contact pin associated with the head frame portion of the interventional RF coil assembly.

FIG. 4 shows a contact pin 100 in greater detail. Each contact pin 100 mechanically and electrically connects the bridge 98 to the arc 96, and more particularly, the upper conductors 142 to the lower conductors 130, to close the loop forming the surface coil. The contact pin 100 includes a lower body portion 148, a middle body portion 150, and an upper body portion 152. The contact pin 100 is preferably formed from a gold-plated copper alloy material. The lower portion 148 connects to the lower contacts 132 with threads or with a medium press fit.

A pointed tip 154 of the lower portion aids in puncturing a sterile drape as described further below. A notch 156 provides a positive stop for the sterile drape. The middle portion 150 of the pin body is surrounded by an insulator 158 that prevents contact with the pin when the coil is in use. The insulator is formed from an easily sterilizable material, and preferably a plastic material such as polyphenylsulfone. The upper body section 152 forms a multiple finger contact that is inserted into the upper contact 144 with a light press fit.

Figure 5:
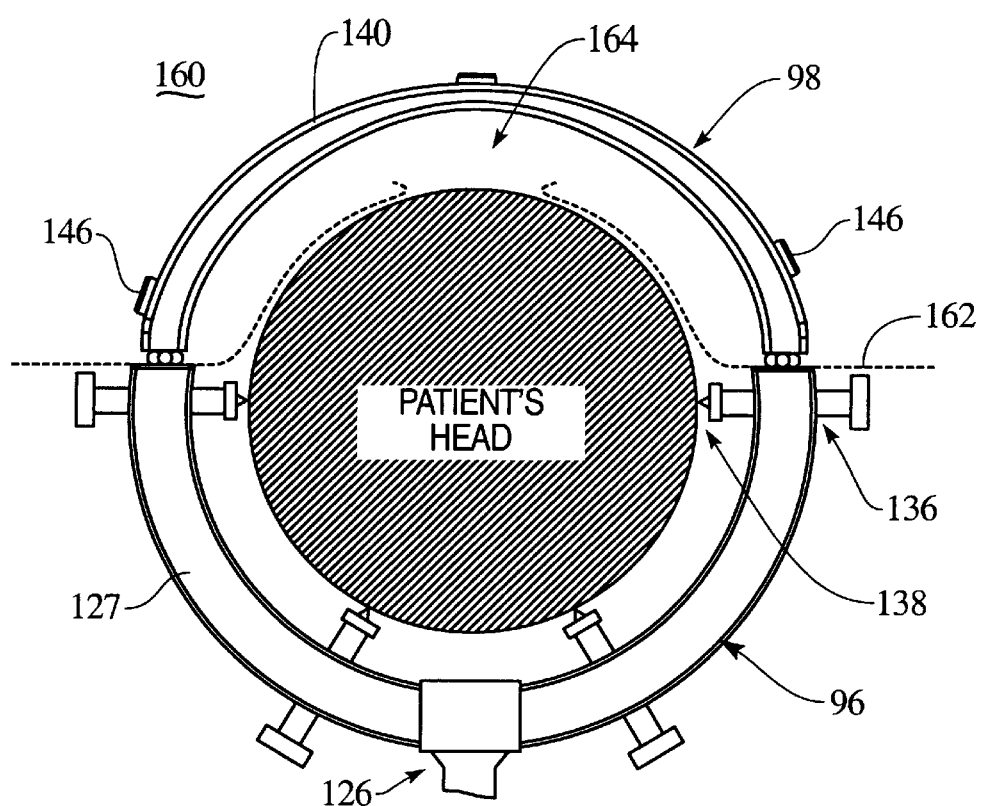
FIG. 5 is an end view of the head frame portion of FIG. 3 being used in a diagnostic imaging procedure.

As shown in FIG. 5, the arc is initially mounted to a patient's head vís-a-vís the screws and pins 136, 138, with the screws 124 threadably engaged with the tapped holes 122. The arc can then be mounted to the base 90 by guiding the screw shanks into engagement with the slots 125 of the shoulder member 116. The screws 124 are then rotated to bring the arc into binding contact with the shoulder member. The head-frame assembly 92 can then be oriented or otherwise positioned relative to the base 90 vís-a-vís the ball and socket joint. Alternatively, the arc 96 can be secured to the base 90 prior to securing the arc to the patient's head. In either case, once the head-frame assembly is oriented as desired, a locking mechanism (not shown) is then used to rigidly secure the bass and socket joint to the base.

With the patient mounted to the arc as described, a sterile field 160 is created around the surgical site by placing a sterile drape 162 over the patient's head and over the upper planar end surfaces of the arc. An aperture 164 through the sterile drape provides access to the surgical site on the patient's head. Sterilized contact pins 100 are then pushed through the drape and screwed or pressed into the lower contacts 132 of the arc. The sterility of the lower half of the contact pins 100 has now been violated, but the flanges in the pins seal the drape down against the arc, preventing contamination of the sterile field. Thus, the arc is used below the drape, outside the sterile field. At this point, the surgery can be performed.

To verify the surgery with an MR scan, the bridge 98, which has been sterilized, is placed over the contact pins 100, thereby closing the conductor loop and creating a functional surface coil as shown in FIG. 5. If additional surgery is required, the bridge 98 can be removed from the contact pins 100 while the pins remain attached to the arc, thereby preserving the sterile field 160 above the drape 162 and gaining access to the surgical site unimpeded by the bridge.

Figure 6:
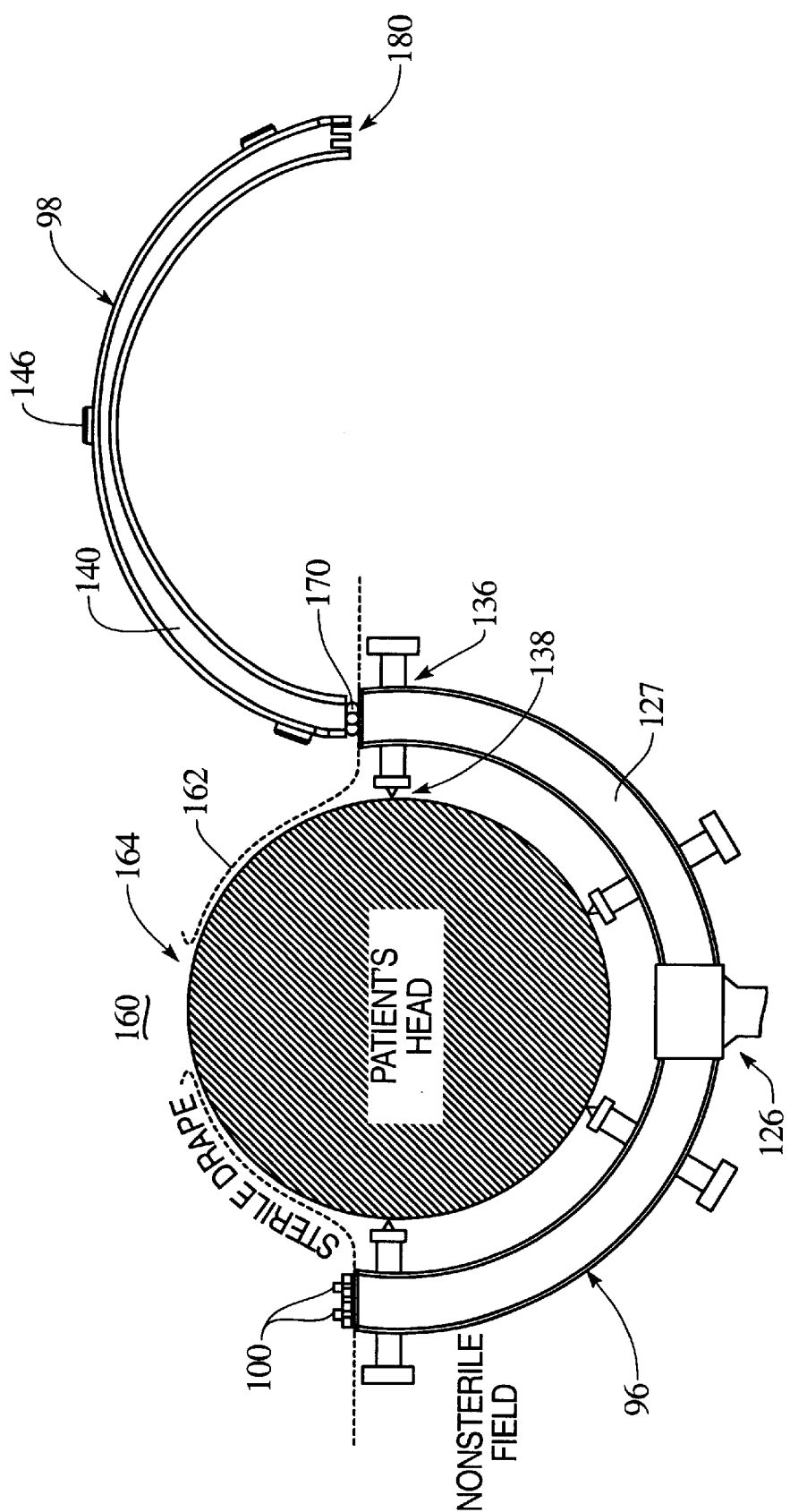
FIG. 6 is an end view of an alternate head frame portion of the interventional RF coil assembly of the present invention.
Figure 7:
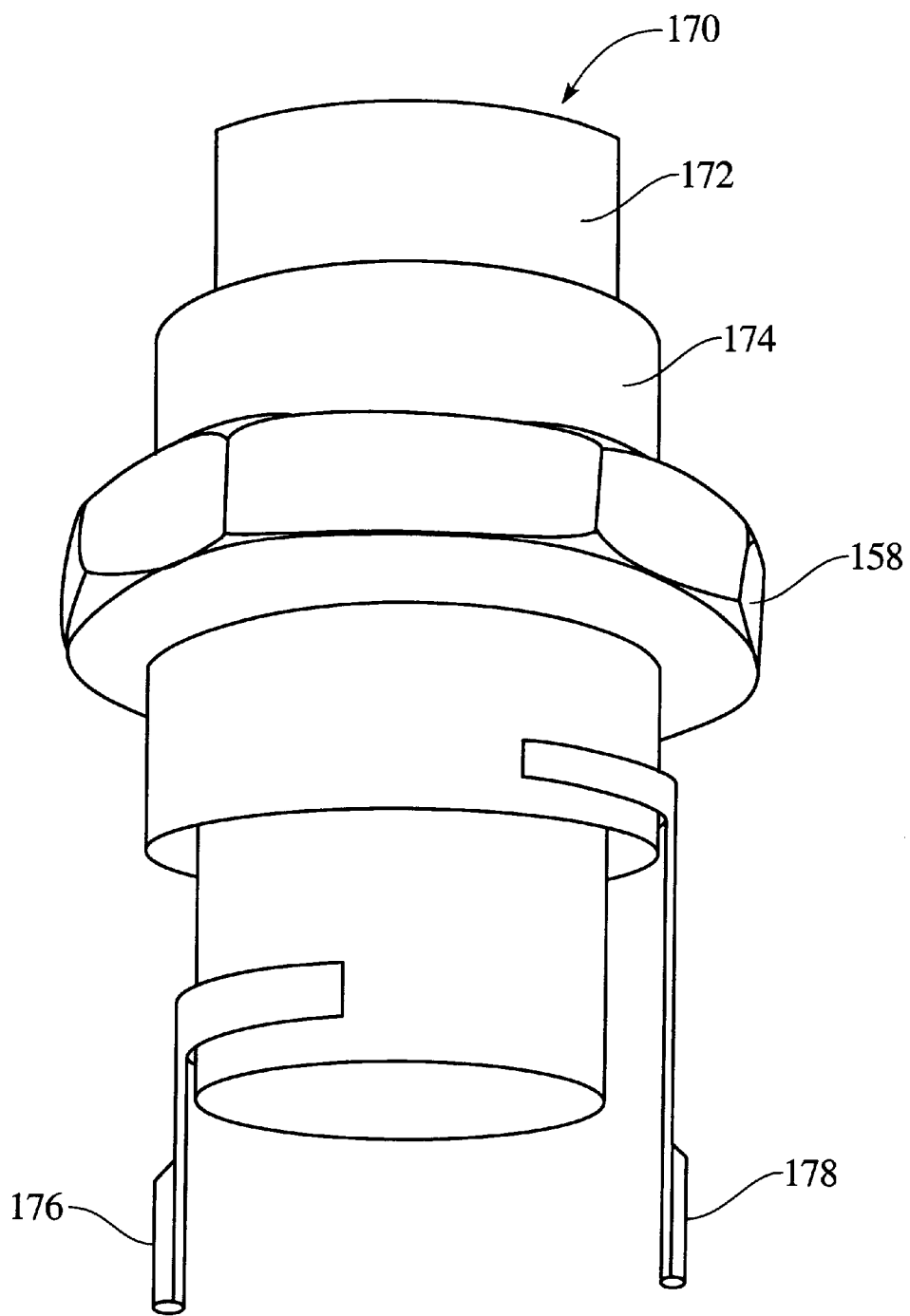
FIG. 7 is a perspective view of a pivot pin associated with the head frame portion of FIG. 6.

Alternatively, as shown in FIG. 6, the bridge 98 can pivot relative to the arc 96 to gain access to the surgical site prior to or after performing an MR scan. In this case, a sterilizable pivot pin 170 can electrically and mechanically connect one side of the bridge to a respective side of the arc. As shown in FIG. 7, an exemplary pivot pin 170 can include coaxial connectors 172, 174 that are press fit or otherwise joined to mutually corresponding coaxial connectors of the bridge to prevent the pivot pin 170 from rotating relative to the bridge. The arc can include slip rings or brushes 176, 178 that electrically contact the coaxial connectors 172, 174, respectively, when the bridge is mated to the arc. Two adjacent contact pins 100 mate with notches 180 at the free end of the bridge to complete the conductor loop when performing an MR scan. Accordingly, the bridge can be pivoted relative to the arc to gain access to the surgical site without having to completely remove the bridge from the arc. And, in order to verify the surgery with an MR scan, the sterilized bridge is pivoted about the arc to make contact with the contact pins 100, thereby closing the conductor loop and creating a functional surface coil.

Figure 8:
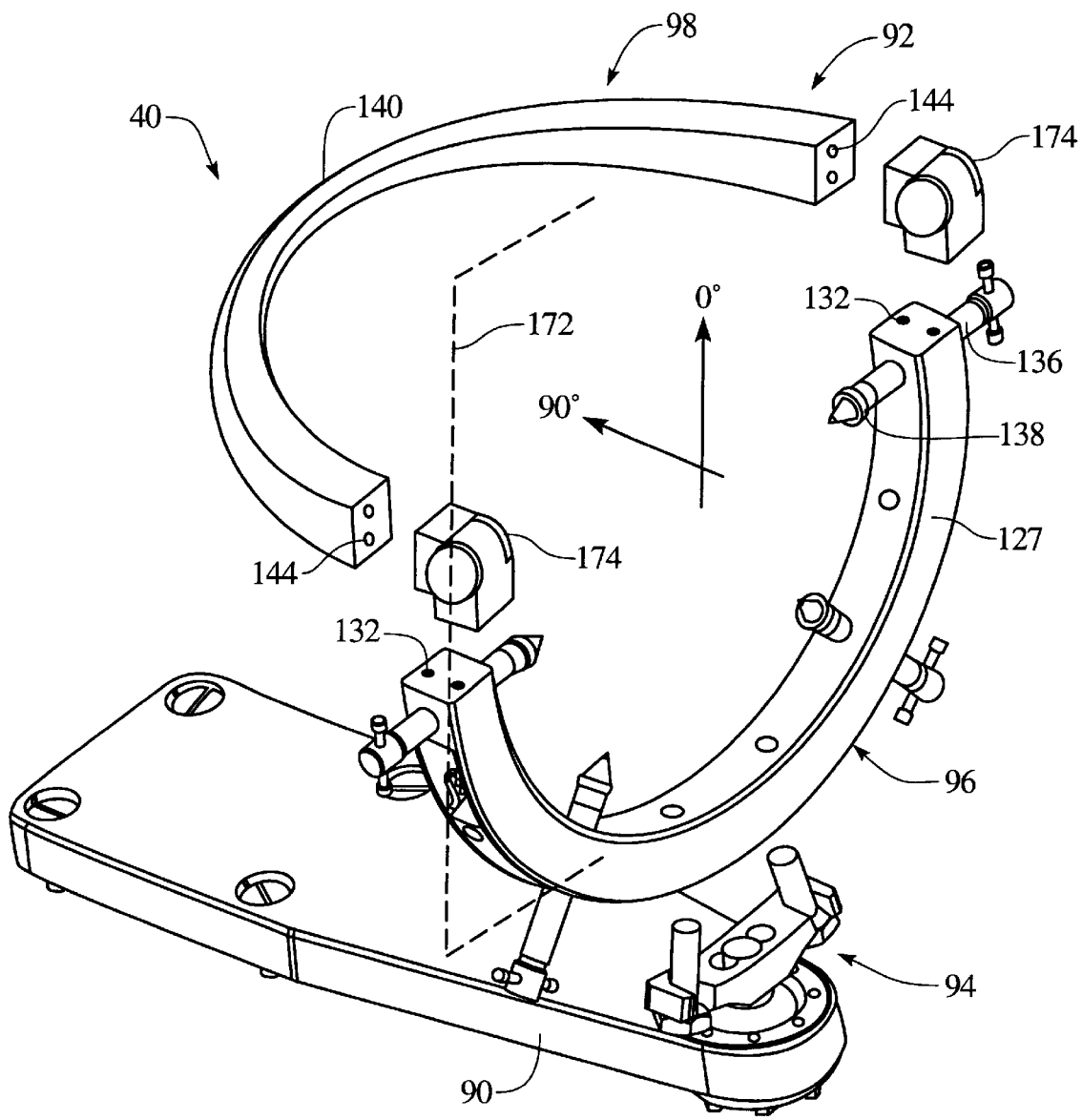
FIG. 8 is a perspective view of an interventional RF coil assembly that incorporates another alternate head frame portion.

In yet another embodiment, as shown in FIG. 8, the bridge 98 can be cantilevered out of a plane 172 of the head frame assembly 92 to gain access to the surgical site prior to or after performing an MR scan. In particular, exemplary, sterilizable, hinge pins 174 mate with the respective upper and lower contacts 144, 132 to electrically and mechanically connect the bridge to the arc. The hinge pins can include a conventional rachet-type mechanism to cantilever the bridge at any angle within the range of about 0° to about 90° relative to the arc. It should be appreciated that the bridge can serve as a hand rest for the surgeon when cantilevered relative to the arc. Further, the bridge can support various surgical accessories such as retractors, hand rests, and biopsy positioners when cantilevered relative to the arc. And, in order to verify the surgery with an MR scan, the sterilized arc is pivoted back into the plane of the head frame assembly 92. In certain situations it may be desirable to perform an MR scan with the bridge cantilevered relative to the arc.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

For instance, it is contemplated that the surface coil formed from the upper and lower conductors 142, 130 can transmit as well as receive RF signals. Further, it is contemplated that surface coil conductors can be adapted for use with a horizontal field MR scanner. In addition, it is contemplated that the sterile drape could be provided with conductive patches pre-inserted into the drape, so that the drape itself can be used to electrically connect the upper surface coil conductors with the lower surface coil conductors. It is also contemplated that active NMR or ESR fiducials can be attached to at least the bridge, wherein the active markers have their own receive coils and channels separate from the imaging coil and receive channel, and are used to determine the position of the coil automatically through software.

Having thus described the preferred embodiments, the invention is now claimed to be:

1. A diagnostic imaging apparatus including a housing defining an examination region, a main field magnet that generates a temporally constant magnetic field through the examination regions a gradient assembly that induces gradient magnetic fields across the temporally constant magnetic field, a patient couch that positions an associated object to be imaged within the examination region, and an interventional head frame assembly that can be positioned within the examination region, the head frame assembly including:
   a head frame removably attached to the patient table, the head frame including at least one first electrical conductor and means for rigidly attaching the head frame to the associated object to be imaged;
   a bridge removably attached to the head frame, the bridge including at least one second electrical conductor; and
   a mount that removably attaches the bridge to the head frame and electrically couples the at least one first conductor to the at least one second conductor to form a surface coil for use in imaging the associated object attached to the head frame.

2. The apparatus of claim 1, wherein the mount includes a plurality of contact pins having lower body portions that i) are adapted to puncture an associated sterile material that is draped across the head frame and ii) engage with electrical connectors associated with the head frame.

3. The apparatus of claim 1, wherein the mount includes at least one pivot pin that permits the bridge to pivot relative to the head frame.

4. The apparatus of claim 1, wherein the mount includes hinge pins that permit the bridge to cantilever relative to the head frame.

5. The apparatus of claim 1, wherein the at least one first conductor provides structural reinforcement to the head frame and carries a current flow of the surface coil.

6. The apparatus of claim 1, wherein the means for rigidly securing includes a plurality of pins threadably engaged with the head frame that cooperate to rigidly secure the associated object to the head frame.

7. A neurosurgical head frame assembly, comprising:
   a base;
   a head frame removably secured to the base, the head frame including at least one first nonconductive beam and a first conductive element that provides structural rigidity to the head frame
   a bridge removably secured to the head frame, the bridge including at least one second non-conductive beam and a second conductive element; and
   a mount that connects the bridge to the head frame thereby coupling the first conductive element to the second conductive element to form an annular surface coil for use in imaging an associated object that is rigidly secured to the head frame.

8. The apparatus of claim 7, wherein the first nonconductive beam includes at least one circumferential slot therein and the at least one first conductive element is bonded within the slot.

9. The apparatus of claim 7, wherein the first non-conductive beam is formed from polyetherimide.

10. The apparatus of claim 7, wherein the at least one first conductive element is formed from a C18200 copper alloy material.

11. The apparatus of claim 7, wherein the at least one second non-conductive beam is formed by injection molding a thermoplastic material from the group consisting of polyetherimide, polyphenylsulfone, and ABS.

12. The apparatus of claim 7, wherein the at least one second non-conductive beam is formed by reaction injection molding a thermoset material from the group consisting of polyurethane and epoxy.

13. The apparatus of claim 7, wherein the at least one second non-conductive beam is formed by liquid resin casting a liquid resin material from the group consisting of polyurethane and epoxy.

14. The apparatus of claim 7, wherein the mount includes a plurality of contact pins having lower body portions that i) are adapted to puncture an associated sterile material that is draped across the head frame and ii) engage with electrical connectors associated with the head frame.

15. The apparatus of claim 7, wherein the mount includes at least one pivot pin that permits the bridge to pivot relative to the head frame.

16. The apparatus of claim 7, wherein the mount includes hinge pins that permit the bridge to cantilever relative to the head frame.

17. A neurosurgical head frame assembly, comprising:

a non-conductive head frame housing including at least one conductive reinforcing member associated therewith;

a non-conductive bridge housing including at least one conductor associated therewith; and a mount that connects the bridge housing to the head frame housing and electrically couples the conductor to the conductive reinforcing member to form a radio-frequency surface coil for use in magnetic resonance imaging of an object that is rigidly secured to the head frame housing, the at least one conductive reinforcing member providing structural reinforcement to the head frame and carrying a current flow of the surface coil.

18. A method of performing neurosurgery with diagnostic imaging guidance, the method comprising:

attaching a head frame housing to a patient's head, the head frame housing having a first conductor associated therewith;

inserting a plurality of pins through a sterile drape positioned over the head frame housing and into engagement with a corresponding plurality of electrical connectors associated with the head frame housing;

attaching a sterile bridge housing to the contact pins thereby coupling a second conductor associated with the bridge housing to the first conductor to form a surface coil;

positioning the patient's head within an examination region of a diagnostic imaging system; and performing a diagnostic imaging procedure utilizing the surface coil.

19. The method of claim 18, further including:

after performing the diagnostic imaging procedure, removing the sterile bridge housing from the contact pins to improve access to a surgical site.

20. The method of claim 18, further including:

after performing the diagnostic imaging procedure, pivoting the sterile bridge relative to the head frame housing to improve access to a surgical site.

21. The method of claim 18, further including:

after performing the diagnostic imaging procedure, cantilevering the sterile bridge relative to the head frame housing to improve access to a surgical site.

22. The method of claim 18, further including:

attaching the head frame housing to a patient couch associated with the diagnostic imaging system.

* * * * *